United States Patent [19]
Diekhans et al.

[11] Patent Number: 6,155,103
[45] Date of Patent: Dec. 5, 2000

[54] DEVICE FOR MOISTURE MEASUREMENT IN HARVESTING MACHINES

[75] Inventors: Norbert Diekhans, Gütersloh; Georg Eggenhaus, Ostbevern; Winfried Wesselmann, Warendorf; Willi Behnke, Steinhagen, all of Germany

[73] Assignee: Claas Selbstfahrende Erntemaschinen GmbH, Harsewinkel, Germany

[21] Appl. No.: 09/167,123

[22] Filed: Oct. 6, 1998

[30] Foreign Application Priority Data

Oct. 9, 1997 [DE] Germany ............................ 197 44 485

[51] Int. Cl.⁷ .............................. G01N 1/20; A01D 41/00
[52] U.S. Cl. ................................ 73/73; 73/863.52; 460/7; 460/114
[58] Field of Search .................... 73/73, 863.52; 56/131; 460/7, 97, 98, 99, 103, 114

[56] References Cited

U.S. PATENT DOCUMENTS

| | | | |
|---|---|---|---|
| 3,270,279 | 8/1966 | Jackson et al. | 324/61 |
| 4,663,978 | 5/1987 | Lenski et al. | |
| 4,994,286 | 2/1991 | Greer | 73/73 |
| 5,173,079 | 12/1992 | Gerrish | 460/7 |
| 5,398,557 | 3/1995 | Shimuzu et al. | 73/863.52 |
| 5,616,851 | 4/1997 | McMahon et al. | |
| 5,664,402 | 9/1997 | Sandvik et al. | 53/384.1 |
| 5,890,961 | 4/1999 | Behnke et al. | 460/114 |

FOREIGN PATENT DOCUMENTS

| | | | |
|---|---|---|---|
| 0 183 643 A1 | 10/1985 | European Pat. Off. | G01N 1/20 |
| 2 123 375 | 11/1971 | Germany | G01N 33/18 |
| 30 45 728 A1 | 7/1982 | Germany | B65G 43/08 |
| 31 18 756 A1 | 12/1982 | Germany | G01N 1/20 |
| 35 38 885 C1 | 6/1987 | Germany | G01N 1/10 |
| 36 12 282 A1 | 9/1987 | Germany | G01N 33/38 |
| 36 21 514 A1 | 1/1988 | Germany | G01N 33/28 |
| 254 865 A3 | 3/1988 | Germany | G01N 1/20 |
| 273 754 A3 | 11/1989 | Germany | G01N 1/20 |
| 41 05 857 A1 | 8/1992 | Germany | G01F 1/86 |
| 41 25 228 C2 | 2/1993 | Germany | G01N 1/20 |
| 42 24 128 A1 | 2/1994 | Germany | G01N 22/04 |
| 195 18 210 C1 | 2/1997 | Germany | G01N 1/18 |
| 195 41 167 A1 | 5/1997 | Germany | G01F 25/00 |
| 1822967 A1 | 6/1993 | Russian Federation | G01N 27/22 |
| 1 464 491 | 3/1975 | United Kingdom | G01N 1/20 |
| 2 150 917 | 7/1985 | United Kingdom | G01N 1/20 |
| WO 89/10548 | 11/1989 | WIPO | G01N 1/20 |

*Primary Examiner*—Hezron Williams
*Assistant Examiner*—Michael Cygan
*Attorney, Agent, or Firm*—Husch & Eppenberger, LLC; Robert E. Muir

[57] ABSTRACT

A device for moisture measurement in harvesting machines, includes means for removing the material to be measured from a stream of crop material, means for supplying the material to be measured to a measuring chamber, an associated moisture sensor, and a means for returning the measured material to the stream of crop material. One improvement is means for compulsory cleaning and/or emptying of the measuring chamber and/or of at least one moisture sensor. As a result, fouling and blockages are avoided.

21 Claims, 7 Drawing Sheets

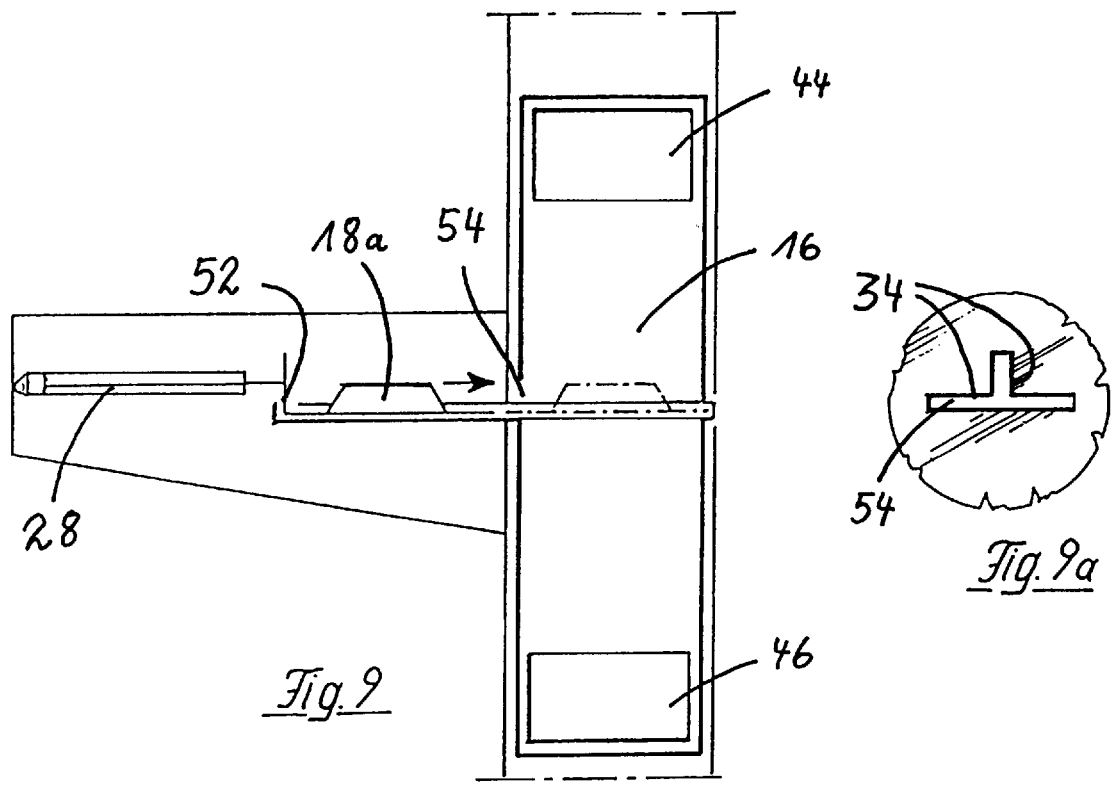
Fig. 9
Fig. 9a
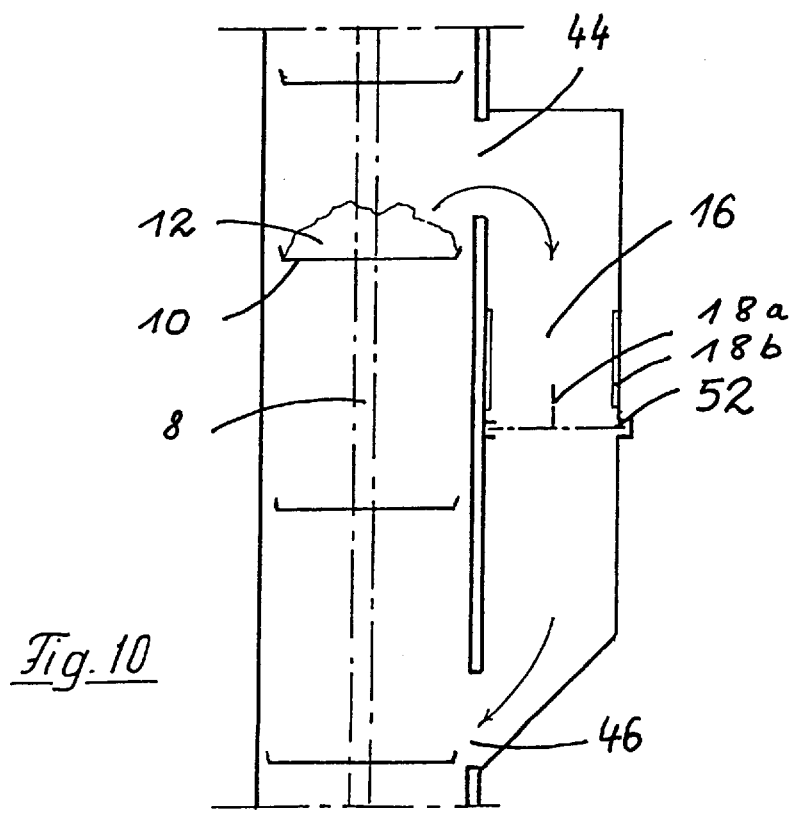
Fig. 10

DEVICE FOR MOISTURE MEASUREMENT IN HARVESTING MACHINES

BACKGROUND OF THE INVENTION

The present invention relates generally to agriculture and, more particularly, to a device for moisture measurement in harvesting machines.

To achieve optimal cultivating of crops and dispensing of fertilizers and plant protection agents according to actual requirements, it is important to determine the yield quantities in respective portions of the cultivated area. The measured yield values of the crop material should be as precise as possible to obtain data from these values for the subsequent produce. The yield is calculated from the stream of material in the harvesting machine, which is in turn related to the mass of crop material dried so as to be capable of storage. Precise determination of the moisture content of the crop material is during harvesting to make the yield correction in the correct position. Furthermore, values can be derived from the measured moisture content of the crop material for adjusting components of a harvesting machine. This also requires high precision of the measured values.

A generic device is known from German Patent Application 41 05 857. The device for moisture measurement shown there serves to correct a quantitative measurement determined by a first measuring device, by a moisture measurement determined by a second measuring device. The second measuring device consists of an overflow vessel. More material to be measured is supplied to the second measuring device in a time interval through an opening than can escape through an opening at the bottom. As a result, under normal harvesting conditions, sufficient filling of the measuring device with continuous exchange of the accruing material to be measured is ensured.

Another moisture measuring device is known from U.S. Pat. No. 5,616,851. There, a device is proposed in which a control flap remains in an "open" position for filling the measuring device, until a sensor indicates sufficient filling of the measuring device.

It is a common feature of both measuring devices that they derive an auxiliary stream from the stream of material for measuring purposes and, after measurement has taken place, return the removed quantity of crop material to the main stream of material. Both devices have the drawback that they soil easily, as a result of which the measured quantities and values are inaccurate, and blockages can occur. The sensors cannot be constantly monitored during continuous harvesting work. Therefore, it is possible for inaccurate values to be measured over a longer period of time owing to soiling or blockage of the measuring chamber or moisture sensor. The inaccurate values are unusable for subsequent evaluations. Furthermore, it is often impossible to subsequently determine the moment when the measured values obtained are erroneous. Thus, not only are the erroneous values disregarded, but also values which are actually correct are lost as well. Harvesting is done only once a year in many regions, therefore, such a loss of data results in a considerable setback in the endeavor to create a reliable database for partially plot-specific applications, especially as data losses can re-occur in subsequent years. Erroneous data which is not noticed can have an adverse effect on the farmer's success. For example, subsequent planning of the use of seed, fertilizers and plant protection agents, using erroneous data can lead to serious misallocations. For these reasons, it is important to carry out moisture measurement as accurately as possible and reliably eliminate all possible sources of error.

Accordingly it is a general object of the present invention to overcome one or more of the deficiencies described above. Another object is to improve the device for moisture measurement in harvesting machines.

SUMMARY OF THE INVENTION

In accordance with the present invention there is provided a harvesting machine for harvesting agricultural crops and having means for removing the material to be measured from a stream of crop material, means for supplying the material to be measured to a measuring chamber, a measuring chamber, an associated moisture sensor, means for return of the measured material to a stream of crop material and a cleaning means for compulsorily emptying the measuring chamber or at least one moisture sensor.

Preferably means are provided which compulsorily empty and/or clean both the measuring chamber and at least one moisture sensor. The characteristic of compulsory emptying or cleaning means that at least emptying or cleaning is brought about by either the form of the means or by the timing of the means. Compulsory emptying and/or cleaning of measuring chamber and moisture sensor ensures that a measurement with new material to be measured can be obtained repeatedly because the measuring chamber is no longer blocked. Also there is a reduction in the risk of smearing the sensor for measuring the filling of the measuring chamber. Such smearing would cause the simulation of constant filling of the measuring chamber. Furthermore, there is a reduction of old crop material clinging to the moisture sensor or to the walls of the measuring chamber falsifying the measurement for the current stream of crop material. In general the reliability of moisture measurement and hence the accuracy and usefulness of the moisture values obtained are clearly increased by the proposed means.

BRIEF DESCRIPTION OF THE DRAWINGS

The invention is described in more detail with the aid of several embodiments shown in the drawings wherein:

FIGS. 9, 9a and 10 show a third embodiment of a device for moisture measurement with a moisture sensor movable laterally into the stream of material to be measured;

DETAILED DESCRIPTION

Figure 1:
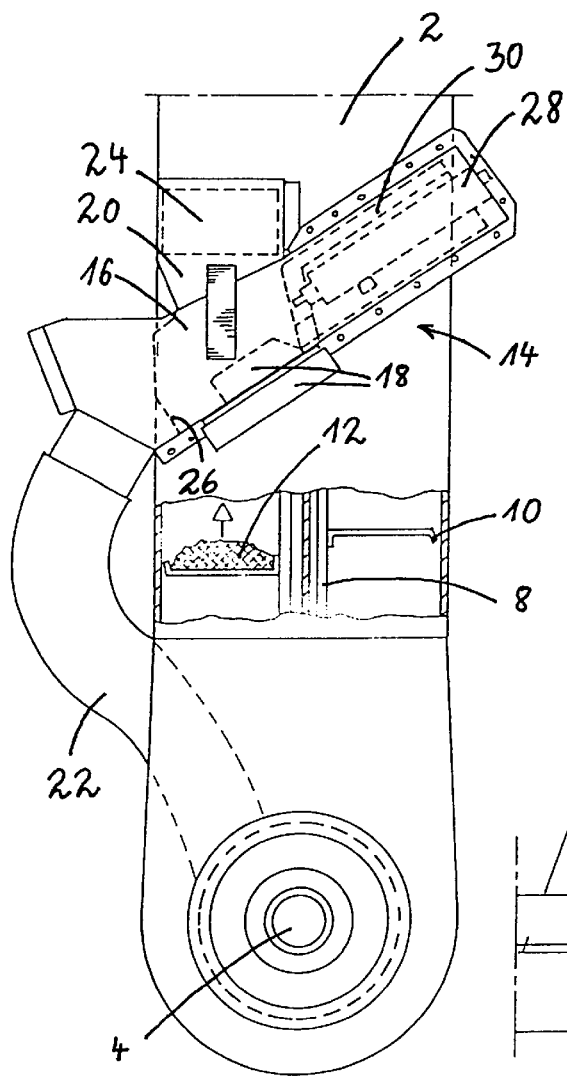
FIG. 1 is an elevational view of a grain elevator of a combine harvester, and having a device for moisture measurement mounted laterally thereon.

FIG. 1 shows a grain elevator 2 of a combine harvester, not shown in more detail, in which a chain 8 with conveyor plates 10, attached thereto, rotates about sprockets 6 mounted on shafts 4. The conveyor plates 10 receive crop material 12 and convey it to a remote discharge station where it is further conveyed or temporarily stored. There the conveyor plates 10 discharge the crop material 12 and return to the feed station to pick up another portion of crop material 12. The succession of a plurality of portions of crop material 12 conveyed by the conveyor plates 10 forms a stream of crop material whose moisture content can be determined by a moisture measuring device 14. The moisture measuring device 14 consists of a measuring chamber 16, a moisture sensor 18, a supply channel 20 and a return channel 22. The crop material 12, whose moisture is to be determined, initially passes through a side opening 24 in the wall of the grain elevator 2, into the supply channel 20 and trickles through the latter into the measuring chamber 16. The measuring chamber 16 is closed by a closure flap 26. After a given time, the measuring chamber 16 is filled to the extent that the moisture sensor 18 can perform reliable measurement of the moisture content of the crop material 12 collected in the measuring chamber 16. At the end of measurement, a hydraulic cylinder 28, acting as a final control element, advances a slide 30 which initially pushes the collected crop material 12 against the closure flap 26 and pushes the latter open. The crop material 12 can then exit the measuring chamber. On advance of the slide 30 to its maximum extended position, the measuring chamber 16 is completely empty. The closure flap 26 geometry may allow for the stripping off of impurities or clinging crop material 12 upon advance of the slide 30 on the front side.

Figure 2:
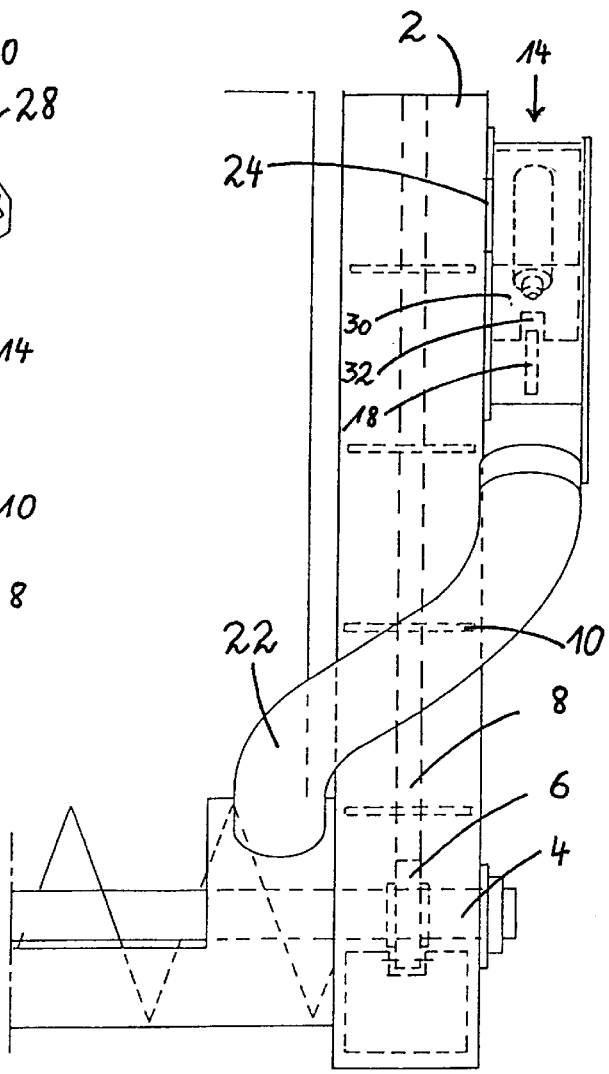
FIG. 2 is a side elevation of the grain elevator and moisture measurement device shown in FIG. 1.

As shown in FIG. 2, the slide 30 comprises a recess 32 whose shape is approximately adapted to the shape of the moisture sensor 18. When the slide 30 travels over the moisture sensor 18, the surfaces of the slide 30, which extend laterally to the moisture sensor 18, strip off accumulations of crop material 12 or other fouling which clings to the moisture sensor 18. In this way the moisture sensor 18 and the measuring chamber 16 in general are cleaned. Upon return of the slide 30, the measuring chamber 16 is again ready to undertake a repeated measurement. The expelled crop material can be reintroduced into the stream of crop material through the return channel 22. As shown in FIG. 2, for example, it can be supplied from above and onto a transverse screw conveyor.

The slide 30 can be operated as a function of various conditions precedent. As a condition, for example, manual switching of the slide 30 can take place. However, an electronic control device, not shown in more detail, can also operate the slide 30 as a function of timing, throughput or crop material or from any combination of these parameters. An electronic regulating system, also not shown in more detail, can optimize a cycle time as required. Also it is conceivable to delay opening of the measuring chamber 16 until the already measured materia has already been conveyed away. Alternatively, measurement can take place so quickly that the already measured material has not yet reached the measuring chamber. It is advantageous, after emptying or cleaning of the measuring chamber 16, to set the measured value of the moisture sensor 18 to a suitable offset value, because deviations from the suitable offset value during the subsequent measurement would result in a corresponding error. Thus it may be sensible to set the offset value to the measured value of moisture in the ambient air, for example 7%.

Figures 3, 4:
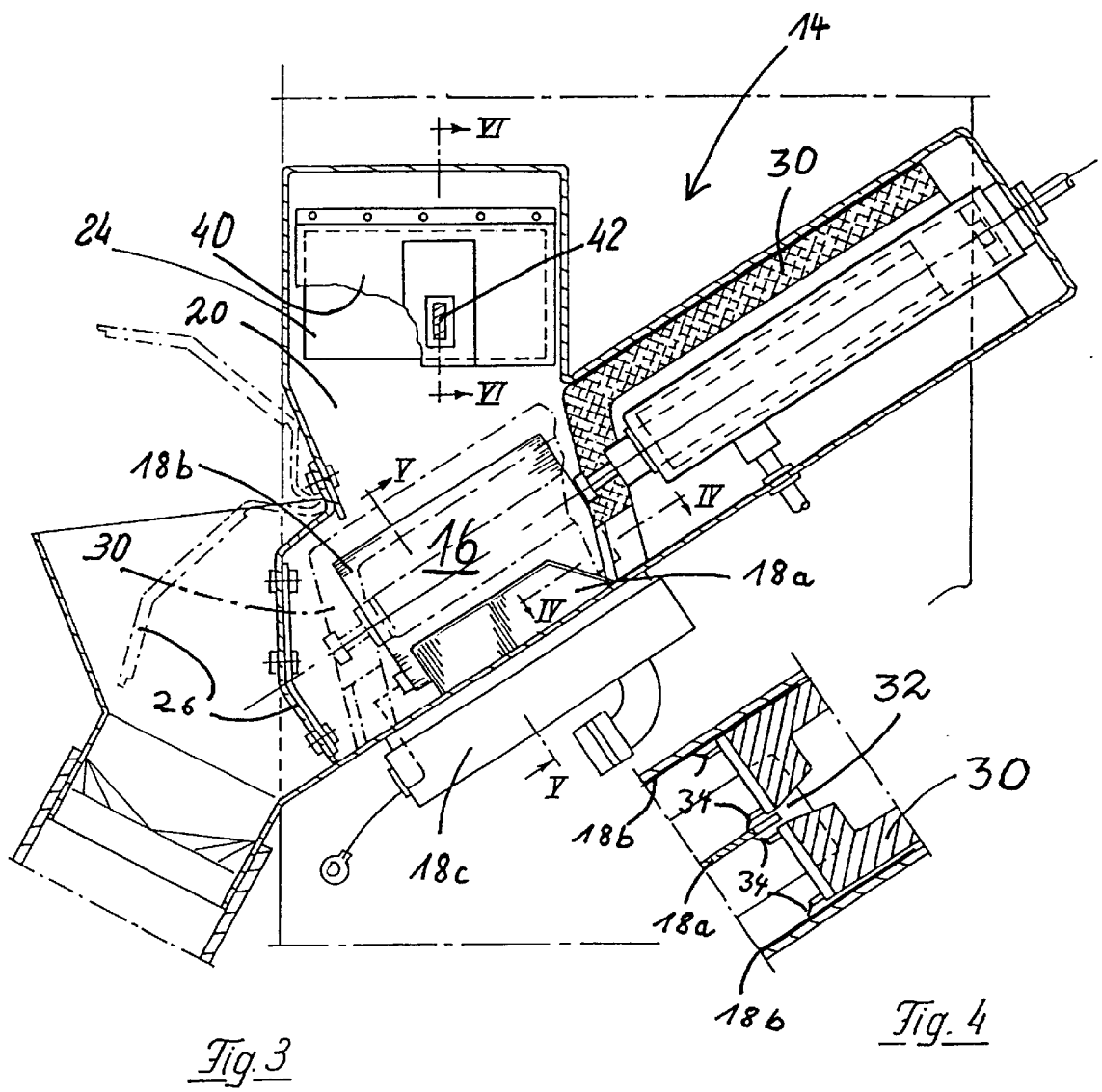
FIG. 3 is a cross-sectional view of the moisture measurement device.
FIG. 4 is a larger scale sectional view taken generally along line IV—IV in FIG. 3.

FIG. 3 shows a more detailed view of the moisture sensor 14 which is arranged in the measuring chamber 16. In the practical example, the moisture sensor 18 consists of a capacitive sensor, but it may optionally consist of other known sensors which are also capable of determining a moisture value of crop material 12. As alternative measuring methods for determining the moisture, apart from capacitance/conductivity, such as the equalizing moisture, the gas pressure, mechanical or electronic infrared drying, microwave absorption, resonance or drying, NIR spectroscopy, NMR spectroscopy or thermoelectrolysis may be used. The capacitive moisture sensor 18 as an example consists of a first electrode 18a, which is located approximately centrally in the measuring chamber 16 and insulated electrically from the side walls thereof. Between the electrode 18a and a counter electrode 18b which is arranged in planar fashion on the side wall of the measuring chamber 16 in the practical example, is the electrical measuring field. If the housing of the measuring chamber 16 is made of a non-conductive material such as plastic for example, a separate electrode 18b must be mounted. If the housing of the measuring chamber 16 is made of an electrically conductive material, it is sufficient to make the housing the conductor. Below the measuring chamber 16, the measuring electronics are arranged in a housing 18c. In addition to the moisture value, the measuring electronics in the housing 18c can determine additional relevant parameters such as the temperature of the crop material 12, which has an effect on the measured moisture value.

The slide 30 is constructed on its upper side in such a way that when its side faces towards the opening 24 and it is in its maximum extended position, it seals off the measuring chamber 16 from oncoming crop material 12. The movement of the closure flap 26 can be transmitted passively from the slide 30, through the crop material 12 and to the closure flap 26. If occasion arises, the closure flap can also be subjected to a spring force which moves the closure flap 26 back into its original starting position. However, a lever assembly, not shown in more detail, connected to the slide 30 or the hydraulic cylinder 28 can also transmit a movement to the closure flap 26. The closure flap 26 may be lifted so far that it allows monitoring and cleaning of the return channel 22. The filling volume of the supply channel 20 when the measuring chamber 16 is closed by the slide 30 should not be greater than the filling volume of the measuring chamber 16. Of course a larger filling volume would allow rapid refilling of the measuring chamber 16. However it should be noted that the pressure of additional crop material 12 located above the measuring chamber 16 can affect the measured moisture value. Also it must be noted that an excessive accumulation of crop material no longer reproduces the true measured value for the currently harvested crop material, but takes into account the measured value for crop material which has already been accumulated shortly after the last emptying or cleaning cycle of the slide 30. Constant filling of the measuring chamber should be ensured for comparability of the measured values obtained. If different layer heights arise in the supply channel 20 due to fluctuating throughput quantities, different measured values can arise when the moisture content is actually identical. Furthermore, it is advantageous if the current angle of inclination of the harvesting machine, which can affect the layer height in the supply channel 20, can also be taken into consideration when the electronic analyzer determines the moisture value.

In FIG. 4 it is easy to see how the slide 30 with its recess 32 can slide over the electrode 18a during a forward movement. With its side surfaces the slide 30 slides over the electrodes 18b. The slide 30 comprises stripping means 34 which can be designed as resilient lips or brushes and simultaneously can guide the slide 30 during its movement in the measuring chamber 16. The electrodes 18a, 18b advantageously serve as guide means for the slide 30. The stripping means 34 strip not only crop material 12 and dirt off the electrodes 18a, 18b, but also prevent the surfaces of the slide 30 from rubbing laterally over the surface of the electrodes 18a, 18b and in this way precludes the electrodes from being damaged or worn down. The interior side surfaces of the recess 32 facilitate lateral alignment of the slide 30 during its return movement as they come in contact with the electrode 18a.

Figure 5:
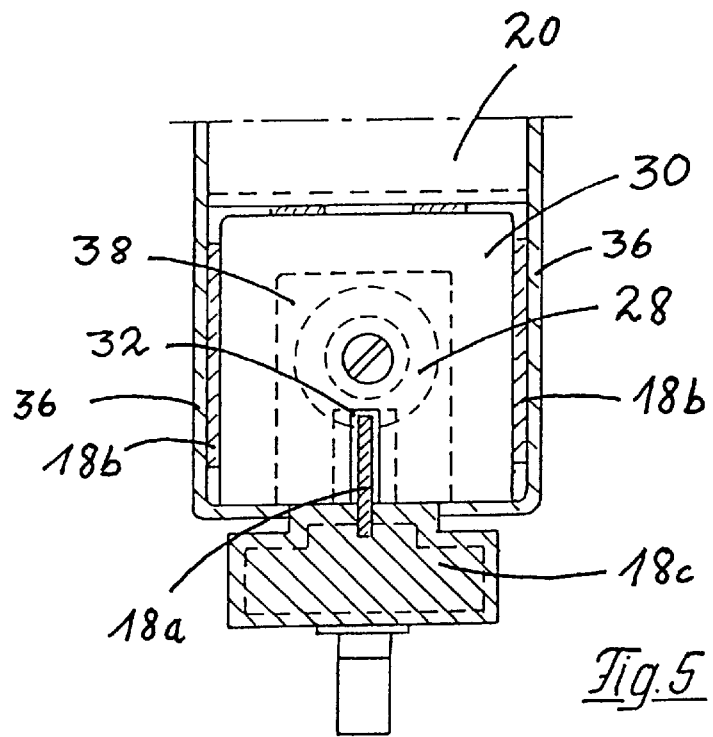
FIG. 5 is a larger scale sectional view along line V—V in FIG. 3.

In FIG. 5, the end face of the slide 30 which with the recess 32 slides over the electrode 18a can be seen in cross-section through the measuring chamber 16. Laterally the slide 30 adjoins the electrodes 18b which are mounted on the side walls 36 of the moisture measuring device 14. The supply channel 20 is shown above the slide 30. The body of the slide 30 encloses a cavity 38 in which is arranged the hydraulic cylinder 28.

Figure 6:
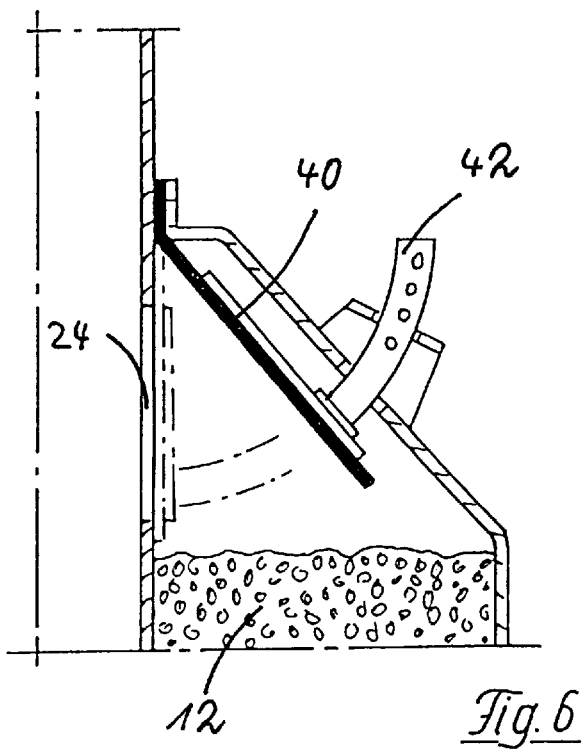
FIG. 6 is a larger scale sectional view along line VI—VI in FIG. 3.

FIG. 6 shows a pivoting closure flap 40 which closes the side opening 24 in the side wall of the grain elevator 2. Pivoting takes place by means of a pivot lever 42 which can be operated manually or by a motor. The closure flap can be operated together with the hydraulic cylinder 28 via a lever assembly to remove an excessive quantity of crop material 12 and force it back into the grain elevator 2 for the purpose of obtaining a uniform measuring portion. However, it may also be sensible to close the moisture sensor 18, for example when no moisture measurement is wanted and unnecessary wear on the sensor is to be avoided. In a preferred embodiment the slide 30 should be stationary when the closure flap 40 is closed.

Figure 7:
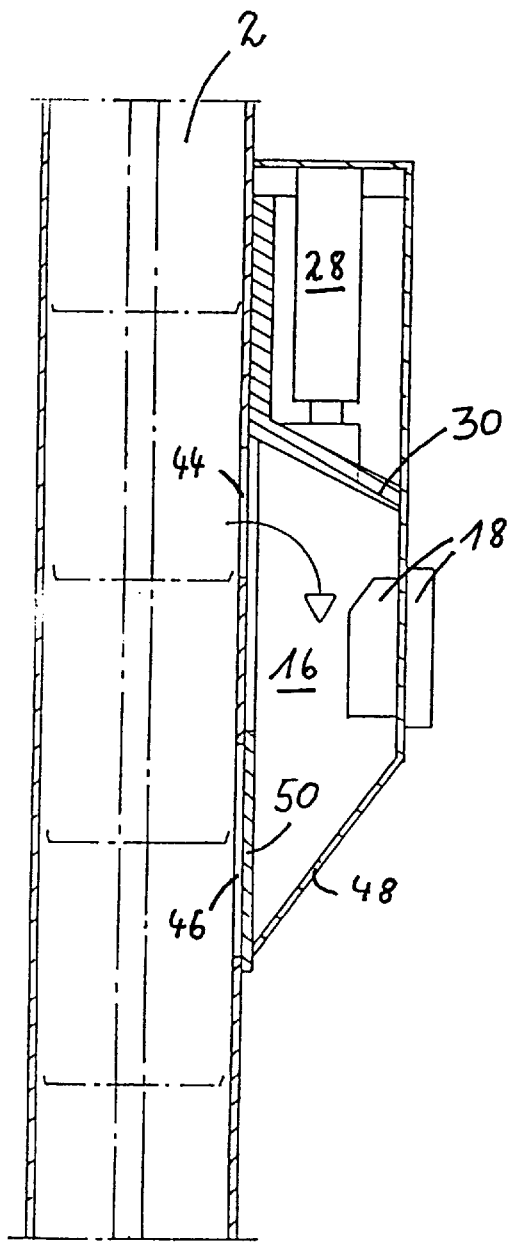
FIG. 7 is a sectional view of a second embodiment of a device for moisture measurement with a vertically movable slide.
Figure 8:
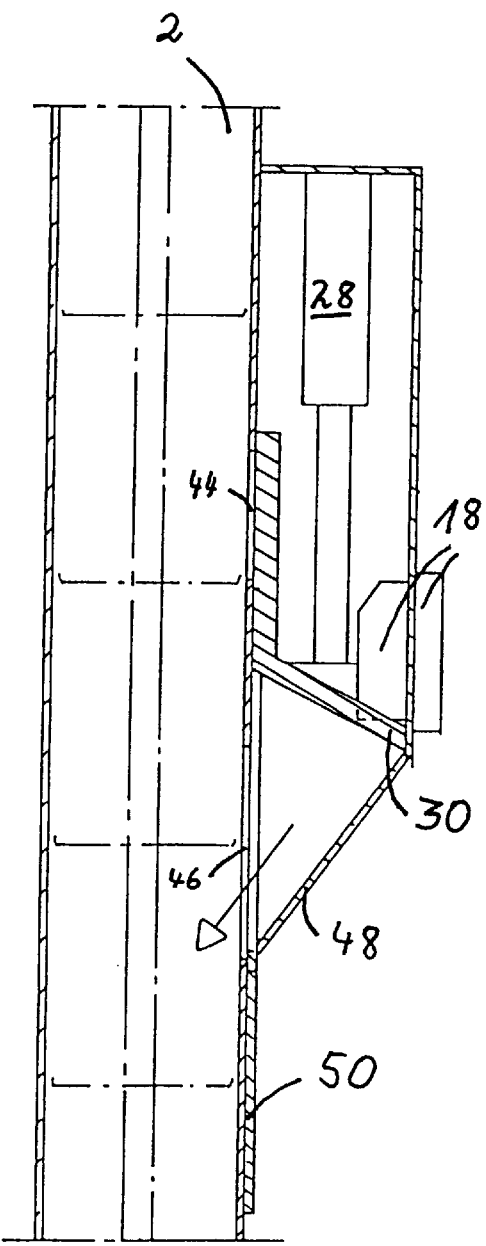
FIG. 8 is a view similar to FIG. 7 but showing another position of compulsory emptying and cleaning means.

In FIGS. 7 and 8 is shown an alternative embodiment in which the measuring chamber 16 is arranged laterally on the grain elevator 2 in such a way that after determination of the moisture value by the moisture sensor 18, the measured material is returned directly into the grain elevator 2. For this purpose an inlet opening 44 and an outlet opening 46 are provided in the side wall of the grain elevator 2; hence these openings are laterally offset from the measuring chamber 16. In order to open and close the supply opening 44 and the outlet opening 46 simultaneously with a control means, the slide 30 is rigidly connected to a closure strip 50. As seen in FIGS. 7 and 8, the measuring chamber 16 has a stationary side wall 48 extending upwardly from adjacent the bottom of the outlet opening 46 at a 30° angle to the grain elevator 2. The closure strip 50 is arranged in such a way that the closure strip 50 in the furthest retracted position of the slide 30 closes the outlet opening 46. In this position of the slide 30 the supply opening 44 is open, so that a portion of material to be measured can be accumulated in the measuring chamber 16. After measurement is completed, the slide 30 with its recess 32 moves over the moisture sensor 18 in the manner previously described. In the process, the closure strip 50 is moved out of the measuring chamber 16 by the slide 30, as a result of which the outlet opening 46 opens and the measured material can run off into the grain elevator. The slide 30 closes the supply opening 44 and, thus, prevents new material from entering the measuring chamber 16. Only when the slide 30 has moved back into a retracted position, can new material to be measured flow into the measuring chamber 16 through the supply opening 44.

Instead of the construction shown in FIGS. 7 and 8, an arrangement can be selected in which the outlet opening 46 is smaller than the supply opening 44, so that the measuring chamber 16 is always full and continuous exchange of the material to be measured is ensured due to absence of the closure strip 50. The slide 30 in such an arrangement is operated only for cleaning and occasional complete emptying of the measuring chamber 16 or of the moisture sensor 18. This prevents impairment of the continuous determination of the moisture value.

In FIGS. 9, 9a and 10 is shown an embodiment in which the electrode 18a is arranged on a carriage 52. The carriage 52, which is operated by a hydraulic cylinder 28 is moved into the measuring chamber 16 and out again. When the carriage 52 has moved into the measuring chamber 16, the material entering the measuring chamber 16 through the supply opening 44 accumulates at the electrode 18a, and a measurement can be made. At the end of measurement, the carriage 52 may be moved back out of the measuring chamber 16, and the accumulated material may exit the measuring chamber 16 again through the outlet opening 46. The carriage 52 with the electrode 18a is moved through an opening 54 located in the side wall of the measuring chamber 16. The geometry of the opening 54 is shaped in such a way that it closely surrounds the outer contour of the carriage 52 or of the electrode 18a, as shown in FIG. 9a. As a result, a stripping and cleaning action occurs when the carriage 52 moves in and out. Additional stripping means 34 can be arranged at the boundary edge of the opening 54, the advantages of which have been shown in more detail above.

Figure 11:
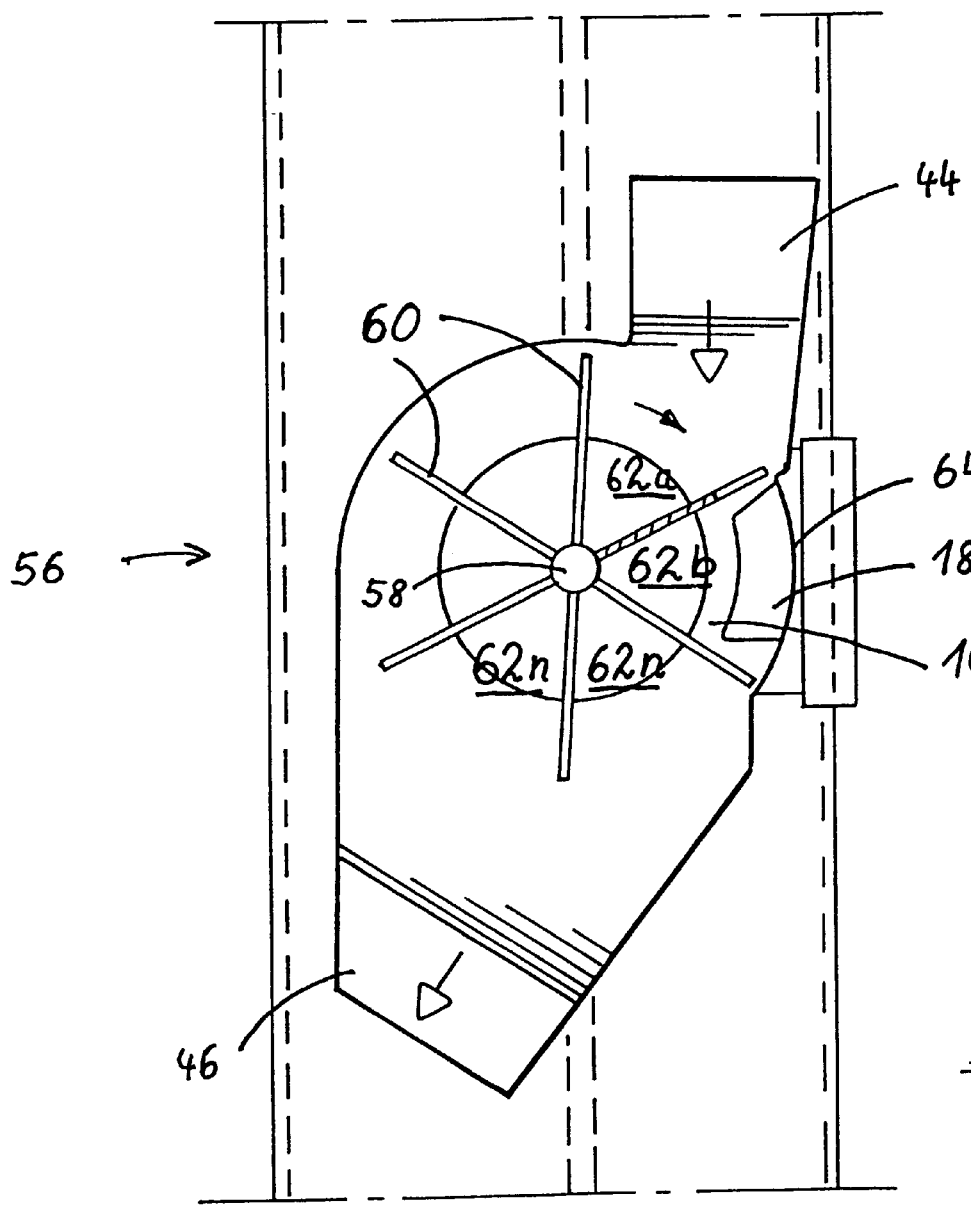
FIG. 11 is an illustration of a fourth embodiment of a device for moisture measurement with a bucket wheel forming the measuring chamber.

In FIG. 11 is shown an embodiment of a measuring device which utilizes a bucket wheel 56. The bucket wheel 56 can be driven by motor, or it is may be set in rotating motion by the force of gravity of the crop material supplied. The bucket wheel 56 consists of a cylindrical body having, in the direction pointing away from its shaft 58, a plurality of bucket walls 60 mounted on the shaft 58 which, in part, spatially define the buckets 62a, 62b, 62n located between them. Crop material 12 supplied through the supply opening 44 drops into the bucket 62a. The rotational movement of the bucket wheel 56 moves the bucket 62a into the region of the wall surface 64 which, at the same time and together with the bucket walls 60 of a bucket 62b, carries the moisture sensor 18 and closes off the measuring chamber 16. At the end of measurement, the crop material 12 can exit the measuring chamber 16 and the region of the bucket wheel 56 via the outlet opening 46. It is worth noting that in this practical example, the point of return leads into the downwardly extending portion of the grain elevator 2 which regularly is not filled with crop material, so that the measured material can be reliably conveyed away. The bucket walls 60 comprise recesses 32, not shown in more detail, whose geometry are coordinated with the moisture sensor 18.

Figure 12:
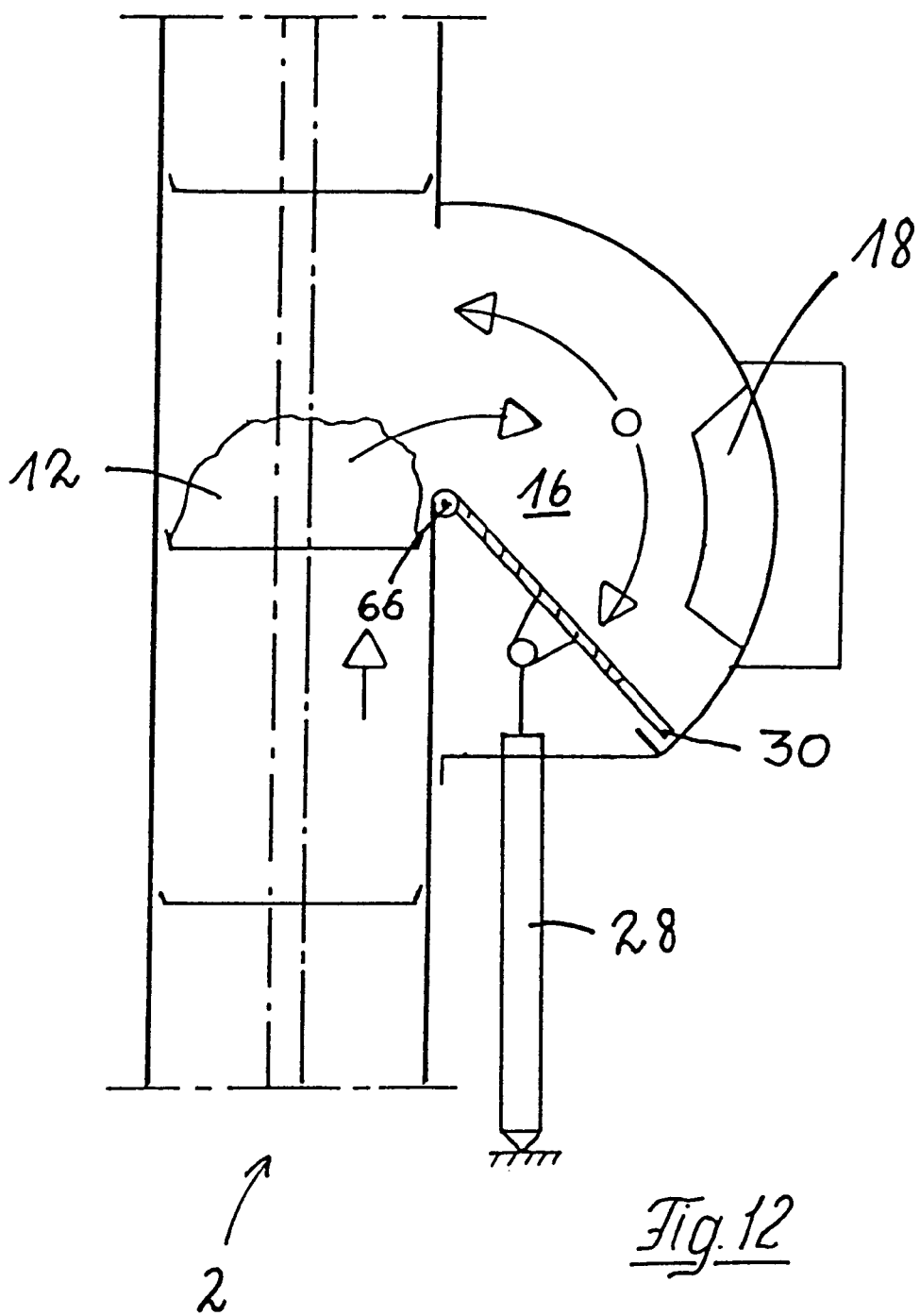
FIG. 12 is a diagrammatic view of a fifth embodiment of a device for moisture measurement with a slide movable about a pivot shaft.

In the FIG. 12 embodiment, the crop material 12 passes into the measuring chamber 16. After carrying out measurement by means of the moisture sensor 18, the hydraulic cylinder 28 moves the slide 30 about the stationary pivot shaft 66. In the process, the measuring chamber 16 is emptied and cleaned and the measured material is forced back into the grain elevator 2.

The described embodiments of the invention are meant as examples. One skilled in the art can adapt the same in such a way that it can also be used in conveying devices other than a grain elevator. Thus, apart from use on a grain elevator of the chain conveyor type, the invention could, for example, also be used on a transverse screw conveyor by attaching a measuring chamber 16, in the form of a cuboid or cylinder, to the side wall of the transverse screw conveyor 68. A slide 30 in the form of a piston moves up and down to fill and empty the measuring chamber. An example of such an arrangement is to found in FIG. 13. This form of a moisture sensor and slide can also be used in other moving conveyor elements such as for a preparation or return floor of a combine harvester. The invention also can be used in impeller-type shafts such as in a field chopper or conveying shafts of a baling press or of a self-loading forage box, or in green fodder equipment such as self-propelled or towed cutter bars, turners or swathers. Furthermore, with respect to the characteristics described, it is not problematic for the expert to replace these by equivalent means familiar to him or to modify the proposed means for certain applications in such a way that the idea of the invention can be used in the specific application.

Other objects, features and advantages will be apparent to those skilled in the art. While preferred embodiments of the present invention have been illustrated and described, this has been by way of illustration and the invention should not be limited except as required by the scope of the appended claims.

We claim:

1. A harvesting machine for harvesting agricultural crops and having means for removing crop material to be measured from a stream of crop material, a measuring chamber, means for supplying the crop material to be measured to the measuring chamber, an associated moisture sensor, means for returning the measured material to the stream of crop material, and emptying means for compulsorily emptying and cleaning the measuring chamber.

2. A harvesting machine according to claim 1, including at least one reciprocatng hydraulic cylinder for moving said emptying means.

3. A harvesting machine according to claim 1, wherein the emptying means at least partially closes the measuring chamber during a movement.

4. A harvesting machine according to claim 1, wherein the emptying means at least partially closes the measuring chamber in an extended position.

5. A harvesting machine according to claim 1, wherein said measuring chamber is at least partially defined by a pivoting closure flap.

6. A harvesting machine according to claim 1, including a supply channel having a filling volume which is not greater than the filling volume of said measuring chamber.

7. A harvesting machine according to claim 6, wherein said supply channel filling volume is less than the filling volume of said measuring chamber.

8. A harvesting machine according to claim 1, including an electronic analyzer which considers a moisture value from the moisture sensor and at least one additional sensor value for correction of the moisture value.

9. A harvesting machine according to claim 1, including guide means for guiding the movement of the emptying means in the measuring chamber.

10. A harvesting machine according to claim 1, wherein a moisture value is determined continuously by the moisture sensor.

11. A harvesting machine according to claim 1, wherein a moisture value is determined discontinuously by the moisture sensor.

12. A harvesting machine according to claim 1, including an elevator feed screw for returning said measured material to the stream of crop material.

13. A harvesting machine according to claim 1, wherein the point of return of said measured material to the stream of crop material is coordinated with the measurement cycle such that previously measured material is precluded from re-entering the measuring chamber.

14. A harvesting machine according to claim 1, wherein the point of return of the measured material leads into the section of a conveying device where there is regularly a minimal amount of crop material.

15. A harvesting machine according to claim 1, wherein after emptying the measuring chamber the measured value of the moisture sensor is in each case set to a suitable offset value.

16. A harvesting machine for harvesting agricultural crops and having a measuring chamber, means for removing a material to be measured from a stream of crop material, means for supplying the material to be measured to the measuring chamber, a moisture sensor associated with the measuring chamber, means for returning the measured material to the stream of crop material, and a rotatable bucket wheel having a plurality of movable bucket walls which at least partially define the measuring chamber.

17. A harvesting machine for harvesting agricultural crops and having means for removing crop material to be measured from a stream of crop material; a measuring chamber; means for supplying the crop material to be measured to the measuring chamber; an associated moisture sensor, means for returning the measured material to the stream of crop material; means for compulsorily emptying the measuring chamber; wherein the means for returning the measured material to the stream includes an outlet opening associated with the measuring chamber; and wherein at least some regions of an underside of the measuring chamber extend upwardly from a bottom of the outlet opening at an inclination of about 30°.

18. A harvesting machine for harvesting agricultural crops and having means for removing crop material to be measured from a stream of crop material, a measuring chamber, means for supplying the crop material to be measured to the measuring chamber, an associated moisture sensor, means for returning the measured material to the stream of crop material, and means for compulsorily emptying the measuring chamber and for cleaning the associated moisture sensor.

19. A harvesting machine for harvesting agricultural crops and having means for removing crop material to be measured from a stream of crop material; a measuring chamber; means for supplying the crop material to be measured to the measuring chamber; an associated moisture sensor, means for returning the measured material to the stream of crop material; means for compulsorily emptying the measuring chamber; a conveying member; and wherein said measuring chamber, in conjunction with said moisture sensor is mounted laterally on the conveying member such that the crop material can pass into the measuring chamber; and including a slide arranged on one side of the measuring chamber which at least partially empties the measuring chamber during operation.

20. A harvesting machine according to claim 19, wherein said slide simultaneously cleans the moisture sensor during at least partial emptying of the measuring chamber.

21. A harvesting machine according to claim 19, wherein said slide is pivoted about a pivot shaft.

* * * * *